United States Patent
Tajima et al.

(10) Patent No.: US 7,500,751 B2
(45) Date of Patent: Mar. 10, 2009

(54) OCULAR FUNDUS PORTION ANALYZER AND OCULAR FUNDUS PORTION ANALYZING METHOD

(75) Inventors: Fumiaki Tajima, Kanagawa (JP); Naoki Miyatake, Kanagawa (JP); Hideaki Sato, Tokyo (JP); Nobuo Matsuda, Yamaguchi (JP)

(73) Assignee: Yokohama TLO Company Ltd., Kanagawa (JP)

( * ) Notice: Subject to any disclaimer, the term of this patent is extended or adjusted under 35 U.S.C. 154(b) by 137 days.

(21) Appl. No.: 10/592,228

(22) PCT Filed: Mar. 10, 2004

(86) PCT No.: PCT/JP2005/004219

§ 371 (c)(1),
(2), (4) Date: Apr. 23, 2007

(87) PCT Pub. No.: WO2005/087087

PCT Pub. Date: Sep. 22, 2005

(65) Prior Publication Data

US 2007/0188705 A1    Aug. 16, 2007

(30) Foreign Application Priority Data

Mar. 12, 2004   (JP) .............................. 2004-071506

(51) Int. Cl.
*A61B 3/14* (2006.01)
*A61B 3/10* (2006.01)

(52) U.S. Cl. ...................... 351/206; 351/221

(58) Field of Classification Search ............... 351/200, 351/205, 206, 221

See application file for complete search history.

(56) References Cited

U.S. PATENT DOCUMENTS

| 5,868,134 | A | 2/1999 | Sugiyama et al. |
| 6,276,798 | B1 | 8/2001 | Gil et al. |
| 6,379,006 | B1 * | 4/2002 | Eikelboom et al. .......... 351/221 |

FOREIGN PATENT DOCUMENTS

| JP | 6-125876 A | 5/1994 |
| JP | 6-154171 A | 6/1994 |

(Continued)

*Primary Examiner*—William C Choi
(74) *Attorney, Agent, or Firm*—Birch, Stewart, Kolasch & Birch, LLP (57) ABSTRACT

An ocular fundus portion analyzer and the method are provided for attaining accurate and quick detection and diagnoses of an ocular fundus defect portion, such as an excavation of an optic disk caused by glaucoma and a macula retinae caused by retinal detachment, by dealing with a large number of single-shot ocular fundus images, for example, taken in physical examinations. It is configured to include an image importing portion for importing an image of an ocular fundus portion taken by a visible radiation or a near-infrared radiation; a pixel data generation portion for generating pixel data including pixel positions and luminance of pixels constituting the image; a local plane gradient image generation portion for generating a three-dimensional image from pixel positions and luminance of the pixel data, obtaining a local approximation plane at any pixel and generating a local plane gradient image from a gradient angle with respect to a control plane of the three-dimensional image; and a display portion for displaying the local plane gradient image.

17 Claims, 6 Drawing Sheets

FOREIGN PATENT DOCUMENTS

| | | |
|---|---|---|
| JP | 7-136123 A | 5/1995 |
| JP | 10-155744 A | 6/1998 |
| JP | 11-151206 A | 6/1999 |
| JP | 2000-245700 A | 9/2000 |
| JP | 2001-145603 A | 5/2001 |
| JP | 2002-543863 A | 12/2002 |
| JP | 2003-190096 A | 7/2003 |

* cited by examiner

OCULAR FUNDUS PORTION ANALYZER AND OCULAR FUNDUS PORTION ANALYZING METHOD

TECHNICAL FIELD

The present invention relates to an ocular fundus portion analyzer and an ocular fundus portion analyzing method, and particularly relates to an ocular fundus portion analyzer and an ocular fundus portion analyzing method for surely detecting an excavation of an optic disk as an area affected by glaucoma, a macula retinae, retrobulbar optic neuritis and maculopathy due to retinal detachment, etc. from an ocular fundus photograph taken in an examination of an ocular fundus for finding eye diseases, such as glaucoma and retinal detachment in particular.

BACKGROUND ART

It is known that, when suffered by glaucoma, an excavation seen as a pale area arises at an optic disk of an ocular fundus; and an existence and stage of the disease are diagnosed by detecting the same. To detect the excavation, a method that a doctor directly observes an ocular fundus image to diagnose and a method that a doctor observes a taken ocular fundus photograph of an affected person have been generally used so far. However, accurate diagnoses and diagnoses on a large number of affected persons in a short time are hard to be attained, and a superior measurement method has been desired.

Under such circumstances, an image analysis of an ocular fundus photograph and more quantitative and accurate diagnoses have become possible as image analysis techniques improve in recent years.

As methods as the above, a method of extracting a pale area of an optic disk based on a threshold calculated from light intensity of the optic disk and diagnosing from an area ratio thereof to the optic disk area (for example, refer to the patent document 1), a method of predicting a visual field defect and a stage thereof by calculating a C/D ratio (a ratio of distance of an edge of the excavation of the optic disk called a cup and an edge of an optic disk called a disk) indicating a size of an excavation of the optic disk from a three-dimensional measurement result of the optic disk of the fundus (for example, refer to the patent documents 2 and 3), a method of extracting a pale area on the optic disk seen on an ocular fundus image used in glaucoma diagnosis by combining an R component image and a chroma image of an RGB image of the ocular fundus (for example, refer to the patent document 4), and a method of obtaining a stereoscopic shape of an optic disk of an ocular fundus from two spectrum images having different wavelengths created from a fundus stereoimage and using the same for the glaucoma diagnosis (for example, refer to the patent document 5), and others are proposed.

The patent document 1: The Japanese Unexamined Patent Publication No. 6-125876

The patent document 2: The Japanese Unexamined Patent Publication No. 11-151206

The patent document 3: The Japanese Unexamined Patent Publication No. 10-155744

The patent document 4: The Japanese Unexamined Patent Publication No. 6-154171

The patent document 5: The Japanese Unexamined Patent Publication No. 2000-245700

DISCLOSURE OF THE INVENTION

Problem to be Solved by the Invention

However, detection and diagnoses of an excavation vary in individuals due to skills and experience of doctors in the conventional method of examining eyes directly by doctors and the detection method of reading an ocular fundus photograph by doctors. Therefore, it has been difficult to detect an excavation in an early stage and diagnose diseased areas accurately and quickly.

Furthermore, even by already proposed methods of detecting a pathologic part from an ocular fundus image by making full use of a variety of analyzing techniques, it has also been difficult to accurately and quickly detect and diagnose ocular fundus defects, such as an excavation of an optic disk due to glaucoma and a macula retinae due to retinal detachment, by dealing with a large number of single-shot ocular fundus photographs taken in physical examinations.

An object of the present invention is to provide an ocular fundus portion analyzer and an ocular fundus portion analyzing method for attaining accurate and quick detection and diagnoses of ocular fundus defects, such as an excavation of an optic disk due to glaucoma and a macula retinae due to retinal detachment, by dealing with a large number of single-shot ocular fundus images taken in physical examinations.

MEANS FOR SOLVING THE PROBLEM

An ocular fundus portion analyzer of the present invention comprises an image importing portion for importing an image of an ocular fundus portion taken by a visible radiation or a near-infrared radiation; a pixel data generation portion for generating pixel data including pixel positions and luminance of pixels constituting the image; a local plane gradient image generation portion for generating a three-dimensional image from pixel positions and luminance of the pixel data, obtaining a local approximation plane at any pixel and generating a local plane gradient image from a gradient angle with respect to a control plane of the three-dimensional image; and a display portion for displaying the local plane gradient image.

Alternately, an ocular fundus portion analyzer of the present invention comprises an image importing portion for importing an image of an ocular fundus portion taken by a visible radiation or a near-infrared radiation; a pixel data generation portion for generating pixel data including pixel positions and luminance of pixels constituting the image; a three-dimensional image creation portion for creating a three-dimensional image of the ocular fundus portion from pixel positions and luminance of the pixel data; and a display portion for displaying the three-dimensional image as an ocular fundus portion shape seen from a plurality of directions.

In the ocular fundus portion analyzer of the present invention, preferably, the image is an image taken by a visible radiation having a wavelength of a red spectrum.

Also preferably, the ocular fundus portion is an optic disk.

Alternately, preferably, the ocular fundus portion is a retinal portion.

An ocular fundus portion analyzing method of the present invention includes a step of importing an image of an ocular fundus portion taken by a visible radiation or a near-infrared radiation; a step of generating pixel data including pixel positions and luminance of pixels constituting the image; a step of generating a three-dimensional image from pixel positions and luminance of the pixel data, obtaining a local approximation plane at any pixel and generating a local plane gradient image from a gradient angle with respect to a control plane of the three-dimensional image; and a step of displaying the local plane gradient image.

Alternately, an ocular fundus portion analyzing method of the present invention includes a step of importing an image of an ocular fundus portion taken by a visible radiation or a near-infrared radiation; a step of generating pixel data including pixel positions and luminance of pixels constituting the image; a step of creating a three-dimensional image of the ocular fundus portion from pixel positions and luminance of the pixel data; and a step of displaying the three-dimensional image as a shape of the ocular fundus portion seen from a plurality of directions.

In the ocular fundus portion analyzing method of the present invention, preferably, an image taken by a visible radiation having a wavelength of a red spectrum is imported in the step of importing an image.

In the ocular fundus portion analyzing method of the present invention, preferably, the ocular fundus portion is an optic disk; and in the step for generating a local plane gradient image, an optic disk shape image is generated from a gradient angle between a local least squares approximation plane and an optic disk control plane at any position on the optic disk.

In the ocular fundus portion analyzing method of the present invention, preferably, the ocular fundus portion is a retinal portion; and in the step for generating a local plane gradient image, an image of a shape of an optic disk defective portion is generated from a gradient angle between a local least squares approximation plane and a control plane of the retinal portion at any position on the optic disk.

In the ocular fundus portion analyzing method of the present invention, preferably, the ocular fundus portion is a retinal portion; and in the step for generating a three-dimensional image, an image of a shape of an ocular fundus portion defective portion is generated by processing by a differential operator at any position on the retinal portion.

EFFECTS OF THE INVENTION

According to the present invention, a shape of an optic disk, retinal and other ocular fundus shape can be precisely and quickly perceived, so that accurate and quick detection and diagnoses of ocular fundus defects, such as an excavation of an optic disk due to glaucoma and a macula retinae due to retinal detachment, become possible even from a large number of single-shot ocular fundus images; thus, remarkable effects can be obtained in the welfare.

EXPLANATION OF REFERENCES

1 . . . red image of optic disk of fundus
2 . . . part with high luminance
3 . . . edge of optic disk
4 . . . excavation of optic disk
10 . . . image generation portion
20 . . . computer
21 . . . image importing portion
22 . . . image data generation portion
23 . . . local plane gradient image generation portion
30 . . . display portion

BEST MODE FOR CARRYING OUT THE INVENTION

Below, an embodiment of an ocular fundus portion analyzer and an ocular fundus portion analyzing method according to the present invention will be explained with reference to the attached drawings.

Figure 1:
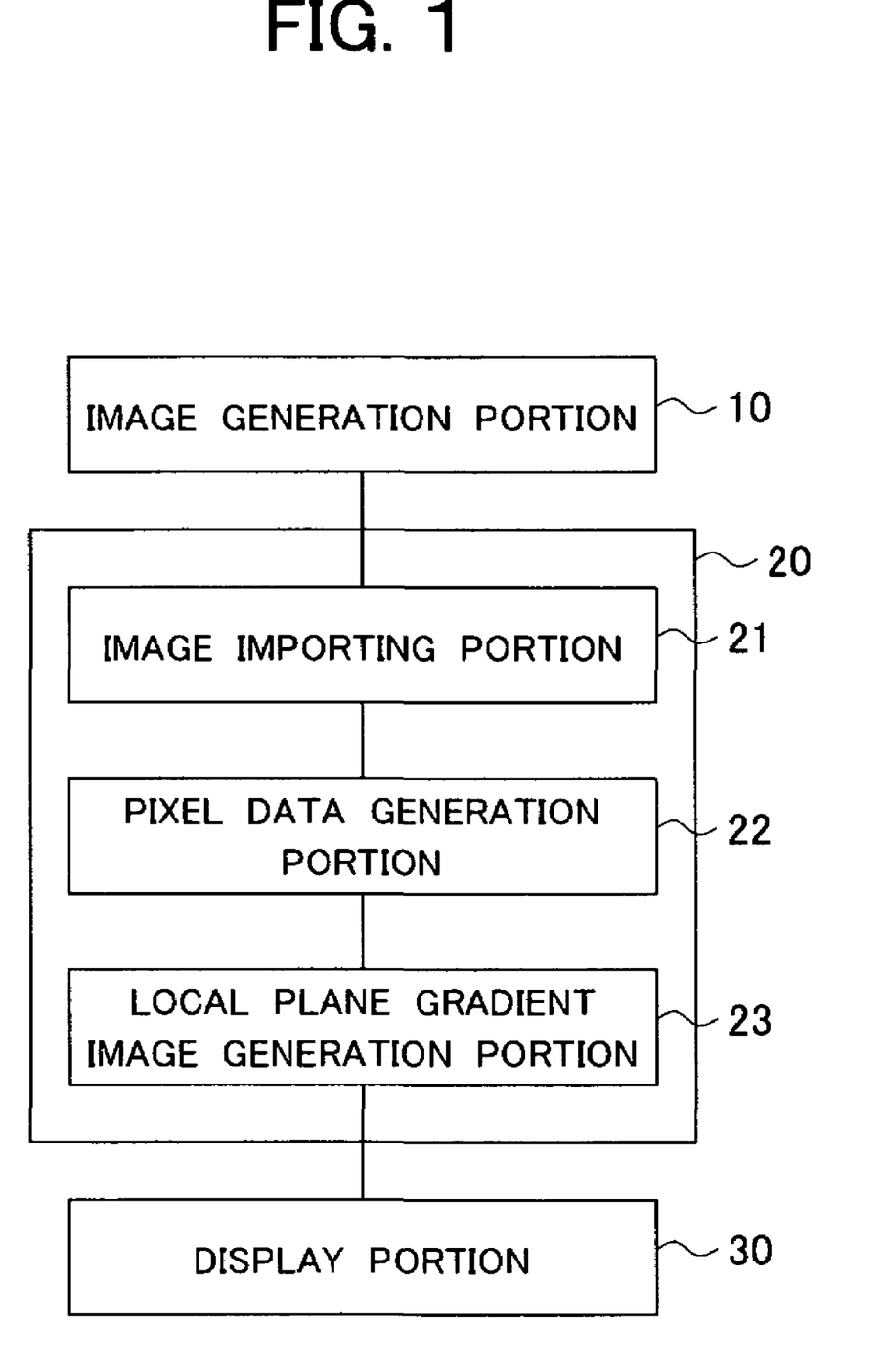
FIG. 1 is a view of the configuration of an ocular fundus portion analyzer according to an embodiment of the present invention.

FIG. 1 is a view of the configuration of an ocular fundus portion analyzer according to the present embodiment.

The ocular fundus portion analyzer according to the present embodiment includes an image importing portion 21, a pixel data generation portion 22, a local plane gradient image generation portion 23 and a display portion 30.

The image importing portion 21 imports an image of an ocular fundus taken by a visible radiation or a near-infrared radiation in the image generation portion 10 having a light source of a visible radiation or a near-infrared radiation, etc. and a CCD camera or other image-pickup portion, stores the same, for example, in a not shown memory portion, etc. and outputs image data to the pixel data generation portion.

The pixel data generation portion 22 generates pixel data including pixel positions and luminance of pixels constituting an image input from the image importing portion 21 and outputs the obtained pixel data to the local plane gradient image generation portion 23.

The local plane gradient image generation portion 23 generates a three-dimensional image from the pixel positions and luminance of the pixel data generated in the pixel data generation portion 22, obtaining a local approximation plane at any pixel, generates a local plane gradient image and outputs the obtained local plane gradient image to the display portion 30.

The display portion 30 graphically displays the local plane gradient image input as above and configured to include, for example, a CRT or other image display portion and/or a printer or other printing portion, etc.

A three-dimensional image creation portion for creating a three-dimensional image of an ocular fundus from pixel positions and luminance of the pixel data may be provided instead of the local plane gradient image generation portion, and an obtained three-dimensional image may be displayed on the display portion as an ocular fundus portion image seen from a plurality of directions.

Note that, for example, the image importing portion 21 may be realized as an input interface of the computer 20, and the pixel data generation portion 22 and the local plane gradient image generation portion 23 may be realized on the computer 20 activating corresponding programs, respectively.

Figure 2:
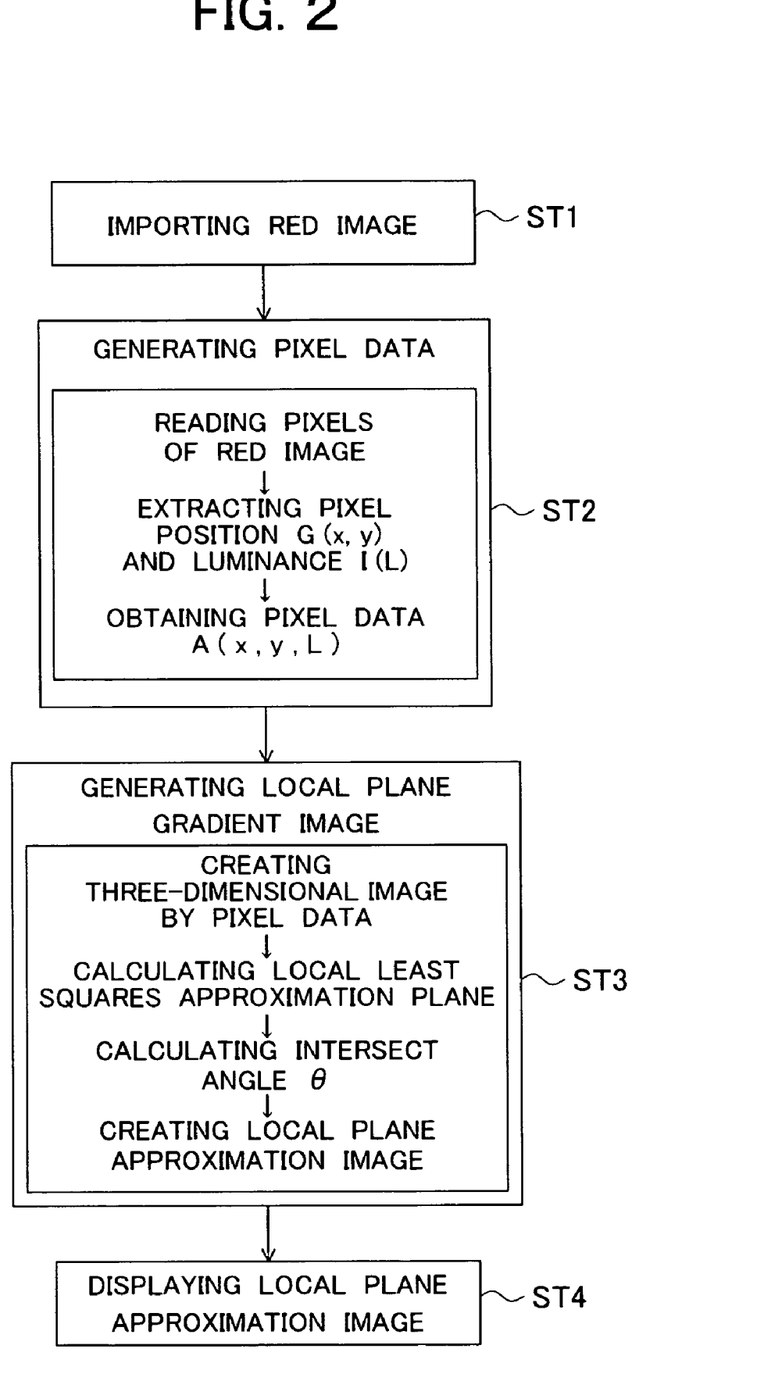
FIG. 2 is a flowchart of an ocular fundus portion analyzing method according to an embodiment of the present invention.

The ocular fundus portion analyzing method according to the present embodiment proceeds as shown in the flowchart in FIG. 2.

Here, the case of an optic disk is used for the explanation, but the same method is used also in the case of a retinal portion or other ocular fundus defects.

First, as the first step ST1, an image of an ocular fundus including an optic disk taken by a visible radiation of the red spectrum is imported. This is performed by the image importing portion 21 of the ocular fundus portion analyzer explained above.

Next, as the second step ST2, pixel data including pixel positions and luminance of pixels constituting an image input from the image importing portion 21 is generated. This is performed by the pixel data generation portion 22 of the ocular fundus portion analyzer explained above.

Figure 3:
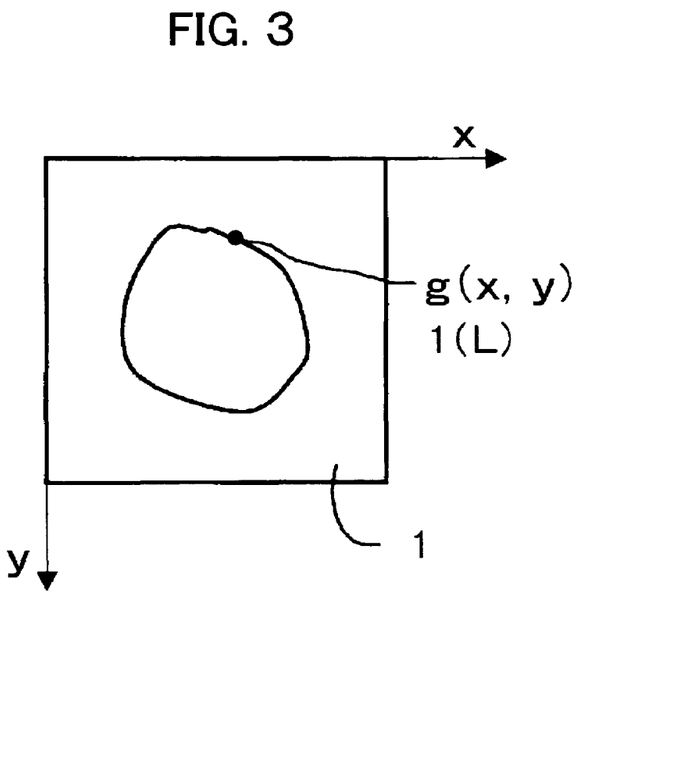
FIG. 3 is an explanatory view showing pixel data.

FIG. 3 is an explanatory view of pixel data. For example, based on the image input from the image importing portion 21, pixel data A(x, y, L) is obtained from positional coordinates g(x, y) and luminance I(L) of pixels constituting an image as shown in FIG. 3 and recorded. This operation is performed on allover the image.

Here, an image taken by a visible radiation of the red spectrum is called a red image, similarly, an image taken by a visible radiation of the green spectrum is called a green image, an image taken by a visible radiation of the blue spectrum is called a blue image, and an image taken by a near-infrared radiation is called a near-infrared radiation image.

In the above explanation, a red image is used for diagnosing an optic disk, because a red image and near-infrared radiation image exhibit stronger penetration to a human body and are capable of taking an image of a deeper inner body comparing with a blue image and a green image taken by a blue light and a green light. However, a blue image and a green image may be used depending on an object; and alternately, a red image, blue image and green image may be analyzed separately and the results may be combined.

Next, as the third step ST3, a three-dimensional image is generated from pixel positions and luminance of the pixel data, a local approximation plate at any pixel is obtained, and a local plane gradient image is generated from a gradient angle with respect to a control plane of a three-dimensional image. This is performed by the local plane gradient image generation portion 23 of the ocular fundus portion analyzer explained above.

Generation of the above local plane gradient image is, for example, performed as explained below.

Namely, in the xyz orthogonal coordinates system, the z-axis indicates luminance and a three-dimensional image of a red image indicating the recorded pixel data A on the xyz orthogonal coordinates system is generated. The entire three-dimensional image is indicated by the positional coordinates and luminance, so that it can be displayed from a variety of view points by using a stereoscopic image display program, etc., so that it becomes easier to recognize a diseased portion and condition of the eye disease. Note that luminance is used as a part of the pixel data here, but a luminance ratio ($L/L_{max}$) obtained by dividing luminance L of each pixel by the maximum luminance $L_{max}$ in the pixels may be also used.

Next, detection of an excavation of an optic disk and a macula retinae due to retinal detachment is performed by using the pixel data A obtained in advance and a three-dimensional image thereof, obtaining a local least squares approximation plane at any point A of the pixel data first, and calculating a gradient angle θ with respect to an xy-plane as a standard horizontal plane of the three-dimensional image.

Here, the local least squares approximation plane is obtained by solving a formula (1) on $A_i \in O (i=1$ to n) on an assumption that a group of pixels near the point A is O.

$$ax_i + by_i + cz_i + d = 0 \qquad (1)$$

Note that "a", "b", "c" and "d" are coefficients.

A gradient angle θ between the local least squares approximation plane and the xy-plane on the three-dimensional image is obtained, for example, by the cosine function formula (2).

$$\theta = \cos^{-1}\{\pm c/(a^2+b^2+c^2)^{1/2}\} \qquad (2)$$

By forming a gradient angle contour drawing with respect to the positional coordinates of corresponding pixels by using the gradient angle θ as an induced variable, a local plane gradient image is generated.

Next, as the fourth step ST4, the obtained local plane gradient image is displayed on the display portion 30.

Here, a local plane gradient image based on a gradient distribution of local least squares approximation plane is used for detecting an excavation of an optic disk and a macula retinae due to retinal detachment, however, a local plane gradient image based on differential operator processing at any point of pixel data, etc. may be also used. Note that a blue image, which is sensitive to an excavation of an optic disk, may be combined with a red image or a near-infrared radiation image, and information of an optic disk and an excavation of the optic disk obtained by relationship of an area ratio and luminance ratio of the optic disk and the excavation of the optic disk and relationship of the number of pixels and luminance of the pixel data may be combined with the above obtained local plane gradient image, so that a more accurate diagnosis on glaucoma and other eye diseases is supported.

EXAMPLES

Below, the present invention will be explained in detail by using FIG. 4 to FIG. 9.

Figure 4:
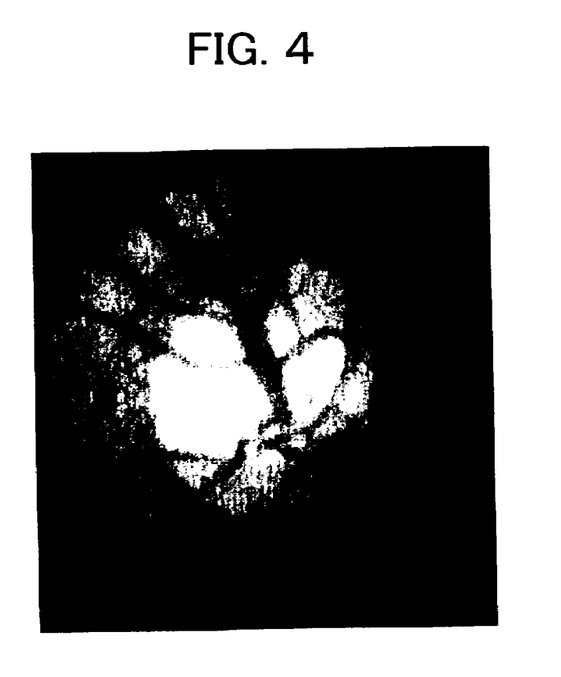
FIG. 4 is a red image of an optic disk of a healthy person taken in an example of the present invention.
Figure 5:
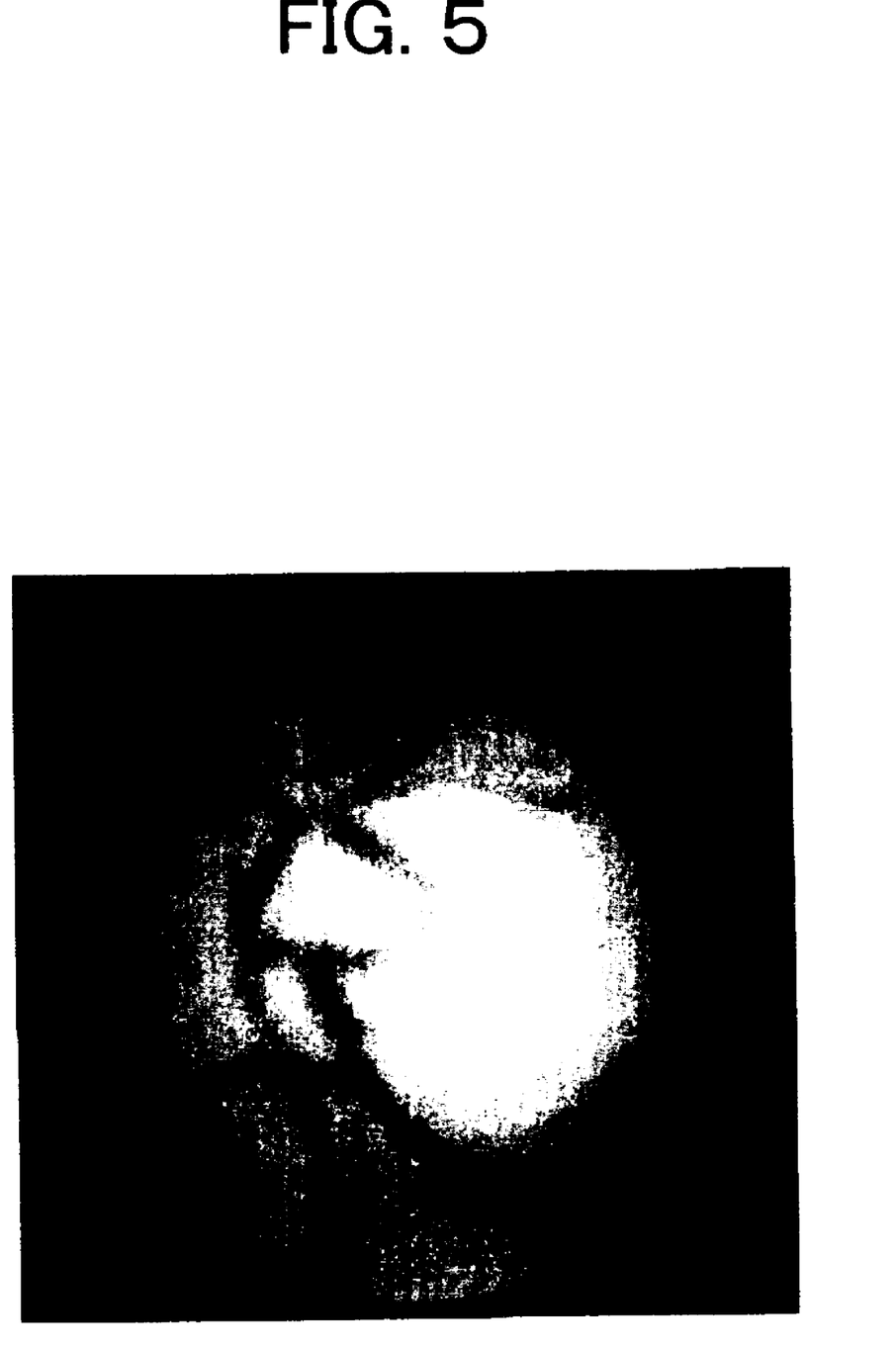
FIG. 5 is a red image of an optic disk of an affected person taken in an example of the present invention.
Figure 6:
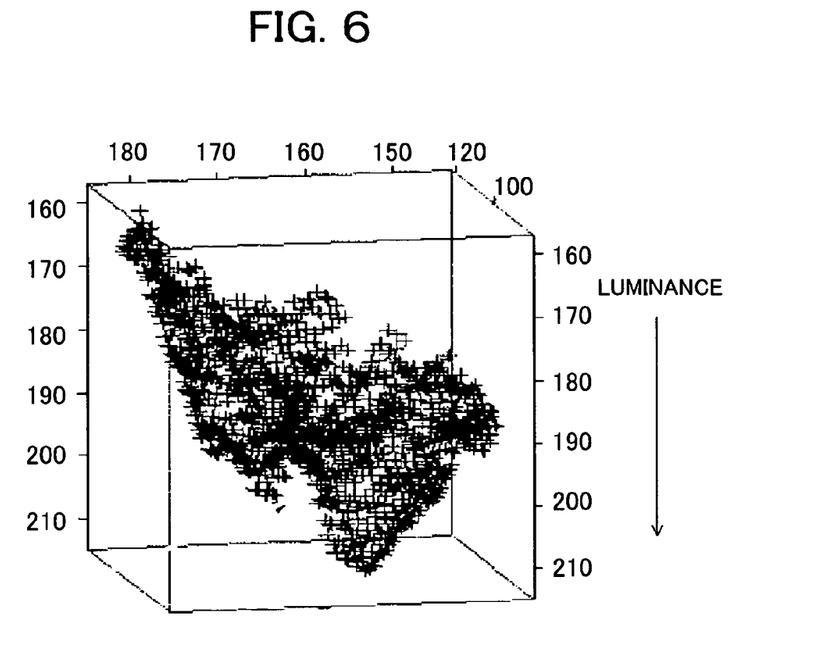
FIG. 6 is a three-dimensional image of an optic disk of a healthy person created from FIG. 4 in the example of the present invention.
Figure 7:
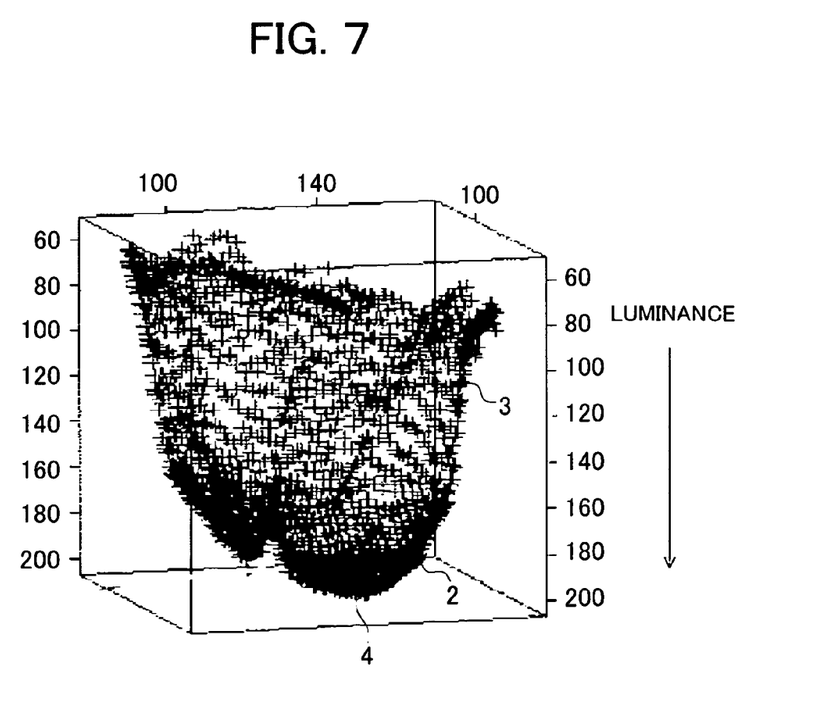
FIG. 7 is a three-dimensional image of an optic disk of an affected person created from FIG. 5 in the example of the present invention.
Figure 8:
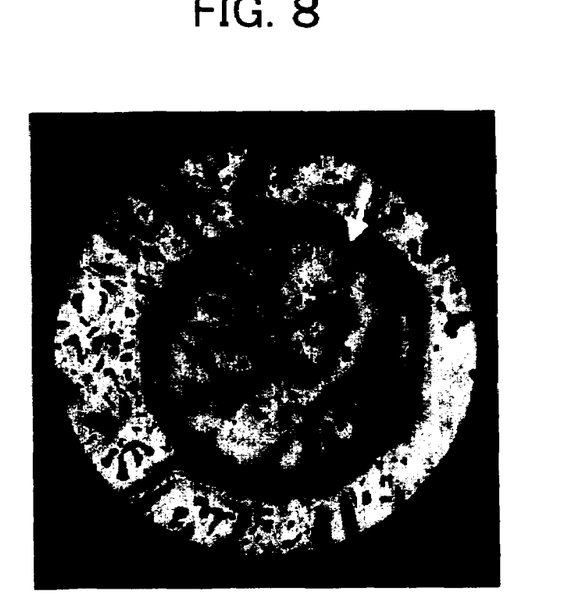
FIG. 8 is a local plane gradient image of a healthy person based on a gradient angle corresponding to a pixel position in the example of the present invention.

FIG. 4 is a red image of an optic disk of a healthy person, and FIG. 5 shows a red image in the case of an affected person. FIG. 6 is a three-dimensional image of an optic disk of the healthy person created from FIG. 4 by using the present invention, and FIG. 7 is that of the affected person and corresponds to FIG. 5. FIG. 8 expresses as a contour drawing a local plane gradient image of a healthy person based on a gradient angle corresponding to pixel positions, and FIG. 9 expresses that of the affected person.

The red image of an optic disk of a healthy person (FIG. 4) obtained by an ocular fundus examination and the red image of an optic disk of an affected person (FIG. 5) were imported to the image analyzer, pixel positions and luminance were measured to create pixel data, and the result was recorded in a memory device. The recorded pixel data was read to a stereoscopic image display program on the personal computer so as to generate a three-dimensional image. An example thereof is shown in FIG. 6 and FIG. 7. FIG. 6 shows an optic disk of a healthy person, and FIG. 7 shows a view of an optic disk of an affected person. It is learnt that, when comparing with the healthy person, the affected person has roundness at a portion 2 with high luminance and has larger gradient of the distribution surface near the optic disk edge portion 3 with low luminance. When comparing the both, an excavation 4 of the optic disk is expressed clearly in the case of the affected person.

Note that luminance used in the present invention varies due to image taking conditions, etc. at ocular fundus examinations, and an absolute value of luminance changes between a healthy person and an affected person, between affected persons and between healthy persons, etc. However, in the present invention, luminance based on diseases is used as a criterion for perceiving changes of a shape of an optic disk to support diagnoses on an existence of diseases and the stage, and a luminance ratio may be used when diagnosing more relatively.

Next, a local least squares approximation plane at any pixel data A is obtained by using n=13, a gradient angle θ with respect to the xy-plane is obtained, and a gradient angle contour drawing was created from positional coordinates (x, y) of a corresponding pixel and the θ.

Figure 9:
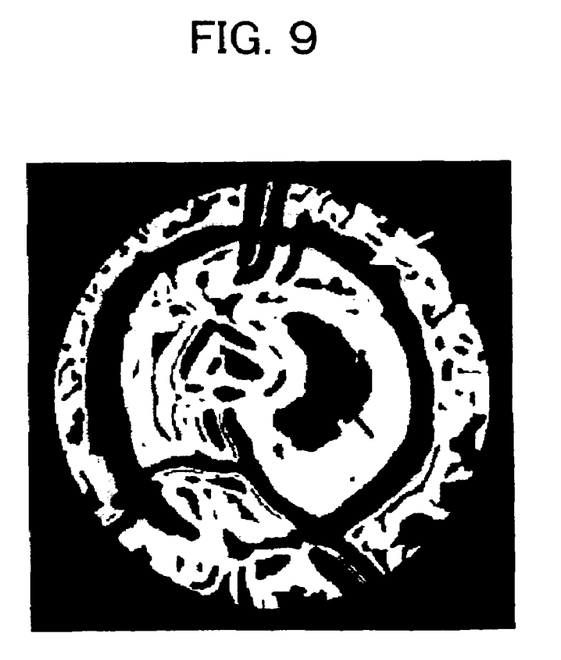
FIG. 9 is a local plane gradient image of an affected person in a gradient angle corresponding to a pixel position in the example of the present invention.

FIG. 8 shows the case of a healthy person, and FIG. 9 shows the case of an affected person. FIG. 8 corresponds to FIG. 4 explained above, and FIG. 9 corresponds to FIG. 5 and FIG. 7.

Parts indicated by black arrows correspond to parts with highest luminance in FIG. 4 and FIG. 5 and parts corresponding to around the bottoms in FIG. 6 and FIG. 7.

When comparing FIG. 8 with FIG. 9, there is almost no small gradient region on the part indicated by the black arrow in FIG. 8 showing the case of a healthy person, while a small gradient region appears as a mass on the part indicated by the black arrow in FIG. 9, so that an existence of an excavation of the optic disk is suggested. Also, a circular part corresponding to the optic disk edge portion indicated by a white arrow is a part with large gradient, and it is spread in the case of the affected person. Furthermore, it is indicated that a position and size of the mass and thickness and clearness of the edge portion can be also used to support diagnoses.

Note that the present invention is not limited to the above embodiment.

For example, it can be applied to a device and method of analyzing other ocular fundus portion than an optic disk and retinal portion.

Also, a light source for taking an image to be imported may be a visible radiation of any spectrum and a near-infrared radiation of any spectrum. A method of using a mixed light of these and separating by using a filter when taking an image, etc. may be also used.

Other than the above, a variety of modifications may be made within the scope of the present invention.

INDUSTRIAL APPLICABILITY

The ocular fundus portion analyzer of the present invention may be applied to an analyzer for diagnosing diseases on an ocular fundus, such as an optic disk and retinal portion.

Also, the ocular fundus portion analyzing method of the present invention may be applied to an analyzing method for diagnosing diseases on an ocular fundus, such as an optic disk and retinal portion.

The invention claimed is:

1. An ocular fundus portion analyzer, comprising:
   an image importing portion for importing an image of an ocular fundus portion taken by a visible radiation or a near-infrared radiation;
   a pixel data generation portion for generating pixel data including pixel positions and luminance of pixels constituting said image;
   a local plane gradient image generation portion for generating a three-dimensional image from pixel positions and luminance of said pixel data, obtaining a local approximation plane at any pixel and generating a local plane gradient image from a gradient angle with respect to a control plane of said three-dimensional image; and
   a display portion for displaying said local plane gradient image.

2. An ocular fundus portion analyzer as set forth in claim 1, wherein said image is an image taken by a visible radiation having a wavelength of a red spectrum.

3. An ocular fundus portion analyzer as set forth in claim 2, wherein said ocular fundus portion is an optic disk.

4. An ocular fundus portion analyzing method, including:
   a step of importing an image of an ocular fundus portion taken by a visible radiation or a near-infrared radiation;
   a step of generating pixel data including pixel positions and luminance of pixels constituting said image;
   a step of generating a three-dimensional image from pixel positions and luminance of said pixel data, obtaining a local approximation plane at any pixel and generating a local plane gradient image from a gradient angle with respect to a control plane of said three-dimensional image; and
   a step of displaying said local plane gradient image.

5. An ocular fundus portion analyzer as set forth in claim 1, wherein said ocular fundus portion is an optic disk.

6. An ocular fundus portion analyzer as set forth in claim 1, wherein said ocular fundus portion is a retinal portion.

7. An ocular fundus portion analyzer, comprising:
   an image importing portion for importing an image of an ocular fundus portion taken by a visible radiation or a near-infrared radiation;
   a pixel data generation portion for generating pixel data including pixel positions and luminance of pixels constituting said image;
   a three-dimensional image creation portion for creating a three-dimensional image of said ocular fundus portion from pixel positions and luminance of said pixel data; and
   a display portion for displaying said three-dimensional image as an ocular fundus portion shape seen from a plurality of conditions.

8. An ocular fundus portion analyzer as set forth in claim 7, wherein said image is an image taken by a visible radiation having a wavelength of a red spectrum.

9. An ocular fundus portion analyzer as set forth in claim 7, wherein said ocular fundus portion is an optic disk.

10. An ocular fundus portion analyzer as set forth in claim 7, wherein said ocular fundus portion is a retinal portion.

11. An ocular fundus portion analyzer as set forth in claim 2, wherein said ocular fundus portion is a retinal portion.

12. An ocular fundus portion analyzing method as set forth in claim 4, wherein an image taken by a visible radiation having a wavelength of a red spectrum is imported in said step of importing an image.

13. An ocular fundus portion analyzing method as set forth in claim 4, wherein:
   said ocular fundus portion is an optic disk; and
   in said step for generating a local plane gradient image, an optic disk shape image is generated from a gradient angle between a local least squares approximation plane and an optic disk control plane at any position on said optic disk.

14. An ocular fundus portion analyzing method as set forth in claim 4, wherein:
   said ocular fundus portion is a retinal portion; and
   in said step for generating a local plane gradient image, an image of a shape of an optic disk defective portion is generated from a gradient angle between a local least squares approximation plane and a control plane of the retinal portion at any position on said optic disk.

15. An ocular fundus portion analyzing method, including:
   a step of importing an image of an ocular fundus portion taken by a visible radiation or a near-infrared radiation;
   a step of generating pixel data including pixel positions and luminance of pixels constituting said image;
   a step of creating a three-dimensional image of said ocular fundus portion from pixel positions and luminance of said pixel data; and
   a step of displaying said three-dimensional image as a shape of the ocular fundus portion seen from a plurality of directions.

16. An ocular fundus portion analyzing method as set forth in claim 15, wherein:
   said ocular fundus portion is a retinal portion; and
   in said step for generating a three-dimensional image, an image of a shape of an ocular fundus portion defective portion is generated by processing by a differential operator at any position on said retinal portion.

17. An ocular fundus portion analyzing method as set forth in claim 15, wherein an image taken by a visible radiation having a wavelength of a red spectrum is imported in said step of importing an image.

* * * * *

UNITED STATES PATENT AND TRADEMARK OFFICE
CERTIFICATE OF CORRECTION

| | |
|---|---|
| PATENT NO. | : 7,500,751 B2 |
| APPLICATION NO. | : 10/592228 |
| DATED | : March 10, 2009 |
| INVENTOR(S) | : Fumiaki Tajima et al. |

It is certified that error appears in the above-identified patent and that said Letters Patent is hereby corrected as shown below:

Title page

Please delete Item "(22) PCT Filed: Mar. 10, 2004" and add Item --(22) PCT Filed: Mar. 10, 2005--.

Signed and Sealed this

Twenty-fifth Day of August, 2009

David J. Kappos
*Director of the United States Patent and Trademark Office*